United States Patent
Bellenger et al.

(10) Patent No.: US 8,722,941 B2
(45) Date of Patent: May 13, 2014

(54) PROCESS FOR PREPARING ALKYL HYDROPEROXIDE COMPOUNDS

(75) Inventors: Fabien Bellenger, Shanghai (CN); Laurent Diguet, Saint Priest (FR); Stéphane Streiff, Lyons (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/508,014

(22) PCT Filed: Nov. 2, 2010

(86) PCT No.: PCT/EP2010/066616
§ 371 (c)(1), (2), (4) Date: Jul. 23, 2012

(87) PCT Pub. No.: WO2011/054809
PCT Pub. Date: May 12, 2011

(65) Prior Publication Data
US 2012/0283482 A1    Nov. 8, 2012

(30) Foreign Application Priority Data
Nov. 5, 2009  (FR) .................................... 09 57834

(51) Int. Cl.
C07C 409/06 (2006.01)
C07C 407/00 (2006.01)

(52) U.S. Cl.
USPC ....................................................... 568/570

(58) Field of Classification Search
USPC ....................................................... 568/570
See application file for complete search history.

(56) References Cited

U.S. PATENT DOCUMENTS

| 4,326,084 A | 4/1982 | Druliner et al. |
| 2008/0070141 A1 | 3/2008 | Sweeney et al. |
| 2009/0076308 A1 | 3/2009 | Veracini et al. |

FOREIGN PATENT DOCUMENTS

| EP | 0092867 A1 | 11/1983 |
| JP | S56-115729 A | 9/1981 |
| JP | S58-192639 A | 11/1983 |
| JP | 63-262481 | 10/1988 |
| JP | 6-310803 A | 11/1996 |
| JP | 9-124594 A | 5/1997 |
| JP | 10-53575 A | 2/1998 |
| JP | 2008-077089 A | 4/2008 |
| RU | 2358962 C2 | 6/2009 |
| WO | 2008/153357 A2 | 2/1998 |

OTHER PUBLICATIONS

International Search Report corresponding to PCT/EP2010/066616 issued Mar. 2, 2011.
Toshio Kamiya, Organic Oxidation Reaction, Theory and Applications of Automatic Oxidation, pp. 187-189, 1973.
Suppes, Galen J., McHugh, Mark, A., "Solvent and Catalytic Metal Effects on the Decomposition of Cumene Hydroperoxide", Industrial & Engineering Chem. Research. vol. 28, No. Jan. 8, 1989. p. 1146-1152.
Römpp Lexikon Chemie, 10th Ed., published by Georg Thieme Verlag, 1999, Stuttgart, DE, p. 4417.
Brandrup, J., et al. eds., Polymer Handbook, Fourth Ed., No. 1, (1999), pp. V/31, V/35, V/41, V/43, published by Wiley-Intersoience, Hoboken, NJ, 6 pages.
"High Performance Fluorompolymer Coating & Linings", (http://www.solvaysites.com/sites/solvayplastics/EN/Solvay%20Plastics%20Literature/BR_Coating_Linings_EN.pdf), Solvay Solexis, Inc., NJ, 2006, 16 pp.
DuPont, "Products by Name", 2013, 2 pp.
DuPont, "Teflon® PFA Resin and Film", (http://www2.dupont.con/Teflon_Industrial/en_US/products/product_by_name/teflon_pfa/), 2013, 7 pp.
Hitech Coatings, "High Performance Coating", (2008), (http://www.hi-techcoatins.net/anti_static_electro_disspative_anti_coating.html), 2 pp.

*Primary Examiner* — Sikarl Witherspoon
(74) *Attorney, Agent, or Firm* — Dentons US LLP

(57) ABSTRACT

A method for making alkyl hydroperoxide compounds, specifically the preparation of cyclohexyl hydroperoxide is described. The preparation of cyclohexyl hydroperoxide by means of the oxidation of cyclohexane by oxygen in a multi-stage reactor or in reactors connected in series is also described. In these methods, the reactor surfaces in contact with the oxidation medium can be protected by a layer of heat-resistant PFA polymer.

7 Claims, 1 Drawing Sheet

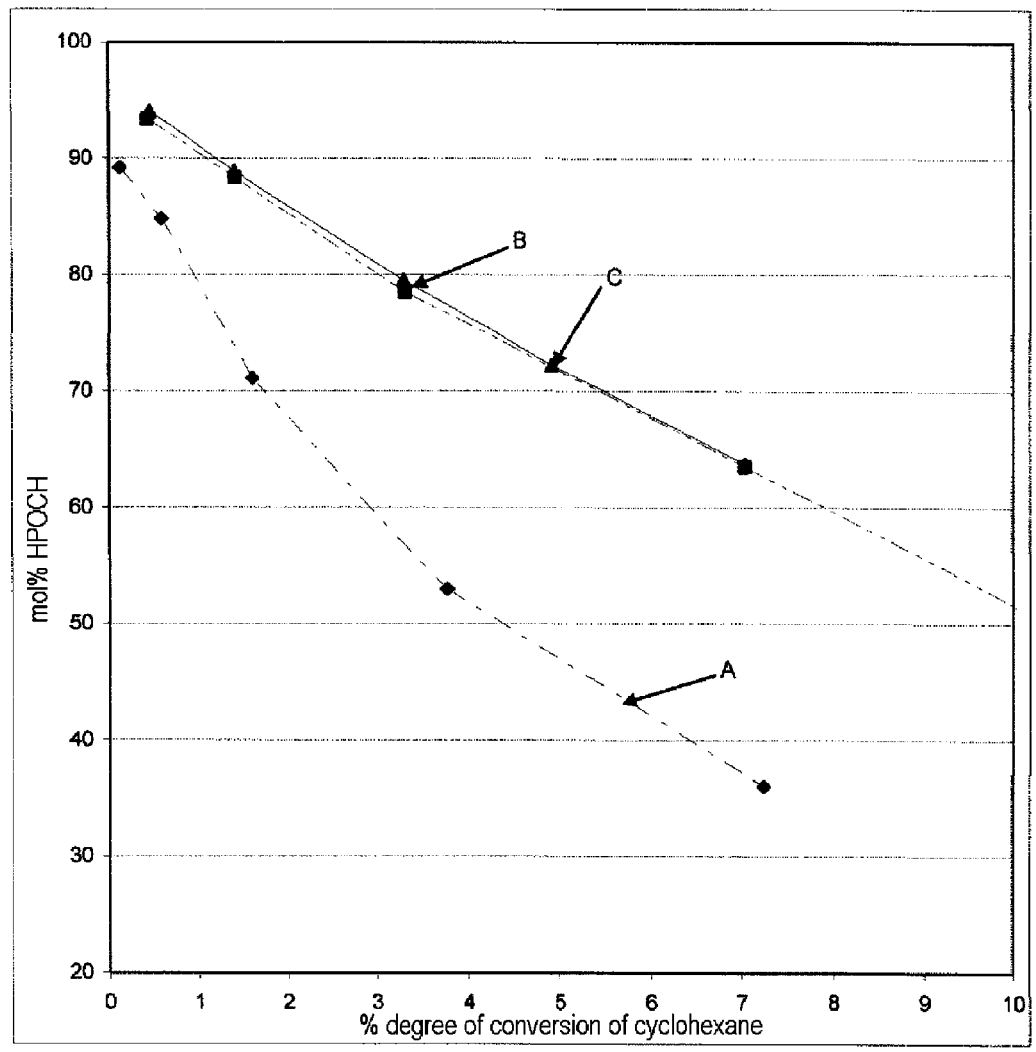

PROCESS FOR PREPARING ALKYL HYDROPEROXIDE COMPOUNDS

CROSS-REFERENCE TO PRIOR APPLICATIONS

This application is a National Stage of PCT/EP 2010/066616, filed Nov. 2, 2010, and designating the United States (published in the French language on May. 12, 2011, as WO 2011/054809 A1; the title and abstract were also published in English), which claims priority of FR 0957834, filed Nov. 5, 2009, each hereby expressly incorporated by reference in its entirety and each assigned to the assignee hereof.

The present invention relates to a process for manufacturing alkyl hydroperoxide compounds, more particularly the preparation of cyclohexyl hydroperoxide.

The invention relates more particularly to the preparation of cyclohexyl hydroperoxide by oxidation with oxygen of cyclohexane in a multistage reactor or reactors mounted in series.

Cyclohexyl hydroperoxide is an intermediate product obtained in the synthesis of adipic acid by oxidation of cyclohexane with oxygen.

Thus, in an industrially exploited process, liquid cyclohexane is oxidized by reaction with oxygen gas in a multistage reactor, at high temperature, to cyclohexane hydroperoxide. After separating out the unreacted cyclohexane, the hydroperoxide is decomposed into cyclohexanol and cyclohexanone, in the presence of a catalyst. The cyclohexanol/cyclohexanone mixture, generally known as "olone", is then oxidized to adipic acid and other diacids with nitric acid. The adipic acid is extracted and purified, advantageously by crystallization.

In this process, it is important to obtain the highest possible yield of cyclohexyl hydroperoxide. This yield depends on the reaction implementation conditions, for instance the temperature and the oxygen concentration.

However, in order to avoid degrading this yield, it is necessary to avoid the decomposition of the cyclohexyl hydroperoxide. Specifically, this compound may decompose rapidly if the medium contains metallic species with high catalytic activity. Such metallic species may often originate from corrosion of the metallic surfaces of the reactor, internal components contained in the reactor and also apparatus or devices attached to the reactors, in which the reaction medium circulates.

To avoid and limit this phenomenon, a process for the pyrophosphatation of metallic surfaces has been proposed for many years, as described in patent U.S. Pat. No. 3,510,526. To obtain this pyrophosphatation, the reactor and its internal components are subjected to a treatment with a pyrophosphate before the start of the oxidation reaction. It is necessary to repeat this treatment periodically, which entails a drop in the operating capacity of the equipment and thus affects the economy of the process.

Moreover, as the operating conditions of the reactor are very harsh (high temperatures and pressure, presence of compounds with high oxidizing power (oxygen, peroxides)), protection of the metallic surfaces with usual protective materials used in chemical reactors cannot be implemented efficiently, pyrophosphatation being virtually the only solution currently used.

One of the aims of the present invention is to propose a solution for efficiently protecting metallic surfaces under the operating conditions of the reactor and that do not require frequent replacement or periodical stoppages of the equipment.

To this end, the invention proposes a process for preparing alkyl hydroperoxide compounds, more particularly cyclohexyl hydroperoxide, comprising the placing of a liquid hydrocarbon, more particularly cyclohexane, in a reactor at a high temperature and at a high pressure in contact with oxygen. According to the invention, the surfaces of the reactor in contact with the medium containing the hydroperoxide comprise a protective coat made of a perfluoroalkoxy polymer, generally referred to as a "PFA polymer".

According to another characteristic of the invention, the reactor may comprise internal components such as plates, stirrers, probes, etc. The surfaces of these components in contact with the medium containing the alkyl hydroperoxide are advantageously protected with a protective coat made of "PFA polymer". Similarly, the devices and equipment attached to the reactor, such as pumps, circulation pipes and cyclohexane flash distillation apparatus, may be advantageously protected with a coating in accordance with the invention, i.e. a PFA polymer coating. Similarly, to avoid decomposition of the alkyl hydroperoxide during a storage phase, the storage device is advantageously protected with a protective coat made of PFA polymer.

A large number of fluoropolymers exist. PFA polymers are a particular family of fluoropolymers. One of the most widely known fluoropolymers is PTFE (poly-tetra-fluoroethylene), sold under the brand name Teflon®.

PFA or perfluoroalkoxy polymers are different from PTFE polymers especially in their meltable nature, i.e. they can be melted and thus formed via the standard processes used with thermoplastic polymers such as injection moulding and extrusion. PTFE therefore cannot be formed easily in equipment, for example to cover the inner walls of reactors. In addition, PTFE has high porosity, which gives rise to phenomena of absorption and desorption of certain chemical products during reaction, such as alcohols, ketones and acids produced by the oxidation of the hydrocarbon. Thus, the use of PTFE presents a large number of drawbacks that are particularly inconvenient in the context of the process of the invention.

These polymers were invented by the company DuPont de Nemours and are especially sold under the trade name Teflon-PFA. Other companies market equivalent polymers, for instance the company Daikin under the trade name Neoflon-PFA, or Solvay under the name Hyflon-PFA, or alternatively the company Gore, and more generally thermally and chemically resistant PFA polymers.

PFA polymers may also comprise mineral or organic fillers to improve their mechanical properties. However, in the context of the invention, these fillers should not comprise metallic elements.

By way of example of PFA polymers that are suitable for use in the invention, mention may be made of the various grades sold by the company DuPont de Nemours under the trade name PFA Ruby Red® or by the company Gore under the trade name Fluoroshield®.

The protective coat made of PFA polymers may be prepared according to the usual methods of deposition of polymer onto a surface or by applying PFA plates or sheets onto the surface to be protected.

Advantageously, the protective PFA coat has a thickness of between 500 µm and 1 mm.

Thus, by way of illustration, a polymer deposition process that may be mentioned is the electrostatic powder coating technique, which consists in applying several coats of polymers and in placing the protected apparatus in an oven to soften or melt the plastic grains so as to obtain a continuous film. This application process comprises a step of preparing the surfaces to be coated so as to free them of grease, clean them and remove surface defects especially at the welds. An example that may be mentioned is the sandblasting process for obtaining a suitable surface state whose quality is indicated by the SA degree defined in standard SIS 05 59 00. After this cleaning, an anchoring priming coat is advantageously applied to the surface. This priming coat may advantageously comprise a PFA polymer. The protective coating is then produced by depositing one or more successive coats of PFA polymers, advantageously by electrostatic spraying of a PFA powder optionally suspended in a liquid.

Other techniques for producing the coating may be used, such as the technique proposed by the company Gore. Thus, in the system marketed by this company under the trade name Fluoroshield®, the process consists in attaching, for example by welding, a grille made of a material such as Inconel® onto the support to be protected and in applying a coat of PFA polymer onto this grille. Thus, the anchoring of the PFA polymer protection is reinforced.

In addition, this protection is advantageously used to protect metal surfaces, especially surfaces made of stainless steel, but it may be used to protect any type of metallic or non-metallic surface.

In one embodiment of the invention for the preparation of an alkyl hydroperoxide described as an example, the process consists in introducing the hydrocarbon such as cyclohexane into the bottom of a tubular reactor, simultaneously with the introduction of oxygen or a gas containing oxygen continuously. However, the invention also applies to processes using other types of reactor, especially with staged introduction of oxygen or introduction of the hydrocarbon into the top of the reactor.

The reaction pressure is between 10 and 30 bar, and the temperature is between 130° C. and 200° C. The oxygen is introduced continuously into the headspace of the reactor at a flow rate of between 10 and 30 Nl/h. For safety reasons, the reaction conditions, especially the residence time in the reactor, are controlled so as advantageously to obtain in the reactor headspace a gas phase containing oxygen at a concentration lower than a critical value, of about 5% by volume, to limit the risks of auto-explosion and auto-ignition with hydrocarbon vapours. However, this characteristic is not obligatory.

The process of the invention makes it possible to limit the decomposition of hydroperoxide formed by the oxidation reaction and thus to improve the reaction yield, by limiting the contact between the reaction medium and the metallic surfaces.

According to the invention, it is also possible to perform a pyrophosphatation on the protective PFA polymer coat.

In addition, the protective PFA polymer coat has a very long service life and can thus improve the economy of the process by reducing the frequency of the stoppages necessary to renew or repair the protection.

Moreover, the protective PFA polymer coat has the advantage of not absorbing or releasing the chemical compounds produced during reaction such as cyclohexanol, cyclohexanone and by-products formed during the reaction, for instance acids, which limits the stoppages for cleaning the reactor.

It also constitutes an efficient barrier to interaction between the metallic walls and the reaction medium, which can limit the decomposition of the hydroperoxide and thus improve the reaction yield.

Furthermore, the protective PFA polymer coat makes it possible to work at high temperature and has better creep resistance, i.e. deformation under a permanent stress. By way of example, under a load of 8.8 MPa (megapascals) at 150° C. for 100 hours, and after 24 hours of relaxation, PFA has a remanent degree of deformation of 10%, whereas this is 34% for PTFE (test performed according to standard ASTM D621).

Other advantages and details of the invention will emerge even more clearly in the light of the examples given below for illustrative purposes.

EXAMPLES

Cyclohexane is placed in a reactor equipped with a self-priming turbomixer and a condenser. The stainless-steel reactor is either unclad, or pyrophosphate-clad or clad with a PFA coat. The reaction medium is heated to 165° C. When the temperature is reached, oxygen at 43% by volume in nitrogen is injected in at a flow rate of 30 Nl/h at a pressure of 30 bar. Samples are taken and analysed by gas chromatography to monitor the formation of cyclohexyl peroxide over time. No difference in selectivity towards HPOCH as a function of the degree of conversion is observed between a pyrophosphate-clad reactor and a reactor clad with a PFA coat; on the other hand, there is a great difference when compared with an unclad reactor.

Reactor Pyrophosphatation Protocol:

An aqueous sodium pyrophosphate solution at 5% by mass is introduced into the stainless-steel reactor. After stirring for 45 minutes at room temperature, the reactor is emptied and then left to dry overnight at room temperature.

Protocol for Producing a PFA Coating in Accordance with the Invention on the Inner Surface of Reactor C:

Preparation of the Support:

The surface to be coated undergoes the usual grease-removal, cleaning and sandblasting treatments. The surface defects and welds are flattened. This treatment may be localized or general to the entire component. The final surface state of the components to be coated is measured and qualified by the SA index defined in standard SIS 05 59 00. This index is 2.5.

Application of the Coating:

Application is performed by spraying a PFA powder sold by the company DuPont as a suspension in water. This application comprises the electrostatic spraying of an anchoring priming coat based on PFA polymer. The reactor is heated to a temperature in the region of 400° C. to allow baking of the priming coat. The baking temperature is generally supplied by the manufacturer of the PFA polymer sold by the company DuPont under the trade name Ruby Red® and depends on the nature of this polymer. A first PFA polymer coat is then applied over the priming coat according to the same technique, and the reactor is then brought to 400° C. again to bake this coat. This operation is repeated as many times as necessary to obtain the desired thickness of the protective coat. For example, depending on the system, electrostatic powder coating is used. The quality and thickness of the protective coat are controlled, especially the homogeneity and the adhesion of the protective coat.

Tests for the production of cyclohexyl hydroperoxide were performed in an unprotected reactor, a pyrophosphatation-protected reactor and a reactor protected in accordance with the invention with a PFA coating, with identical operating conditions described above.

The mole percentage of cyclohexyl hydroperoxide (HPOCH) produced was measured for different degrees of conversion of cyclohexane. The results obtained are collated in FIG. 1, which represents the variation in the molar amount of HPOCH produced as a function of the degree of conversion of cyclohexane for the three reactors used:

Curve A: test in an unprotected stainless-steel reactor
Curve B: test in a pyrophosphatation-protected stainless-steel reactor
Curve C: test in a stainless-steel reactor protected with a PFA coating in accordance with the invention.

These results show that the coating in accordance with the invention affords protection equivalent to that obtained with the pyrophosphatation process.

The invention claimed is:

1. A process for preparing an alkyl hydroperoxide, the process comprising placing a liquid hydrocarbon in a reactor at a high temperature in contact with oxygen, wherein a surface of the reactor in contact with a medium comprising the hydroperoxide comprises a protective coat made of a perfluoroalkoxy (PFA) polymer.

2. The process as defined by claim 1, wherein internal components are arranged in the reactor, and a surface of the components in contact with the medium containing the alkyl hydroperoxide comprises a protective coat made of a perfluoroalkoxy (PFA) polymer.

3. The process as defined by claim 1, wherein the protective coat has a thickness of from 500 µm to 1 mm.

4. The process as defined by claim 1, wherein the protective coat is obtained by depositing PFA polymer.

5. The process as defined by claim 1, wherein the protective coat is formed by a PFA film applied onto the surface to be protected.

6. The process as defined by claim 1, wherein the protective coat is produced by arrangement and juxtaposition of a PFA plate on the surface to be protected.

7. The process as defined by claim 1, wherein the alkyl hydroperoxide is cyclohexyl hydroperoxide, and the hydrocarbon is cyclohexane.

* * * * *